United States Patent
Gessner et al.

(10) Patent No.: US 9,493,422 B2
(45) Date of Patent: Nov. 15, 2016

(54) QUINOID RYLENEDICARBOXIMIDES AS IR ABSORBERS

(75) Inventors: Thomas Gessner, Heidelberg (DE); Helmut Reichelt, Neustadt (DE); Klaus Muellen, Cologne (DE); Zhihong Liu, Qingdao (CN); Chen Li, Mainz (DE)

(73) Assignees: BASF SE, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 833 days.

(21) Appl. No.: 12/993,739

(22) PCT Filed: May 20, 2009

(86) PCT No.: PCT/EP2009/056157
§ 371 (c)(1),
(2), (4) Date: Nov. 19, 2010

(87) PCT Pub. No.: WO2009/141387
PCT Pub. Date: Nov. 26, 2009

(65) Prior Publication Data
US 2011/0076779 A1    Mar. 31, 2011

(30) Foreign Application Priority Data
May 23, 2008 (EP) .................... 08156849

(51) Int. Cl.
*C07D 221/18* (2006.01)
*G01N 31/22* (2006.01)
*C09B 5/62* (2006.01)

(52) U.S. Cl.
CPC .............. *C07D 221/18* (2013.01); *C09B 5/62* (2013.01); *G01N 31/221* (2013.01); *Y10T 428/31504* (2015.04); *Y10T 428/31678* (2015.04); *Y10T 428/31815* (2015.04); *Y10T 428/31993* (2015.04)

(58) Field of Classification Search
None
See application file for complete search history.

(56) References Cited

U.S. PATENT DOCUMENTS

| | | |
|---|---|---|
| 5,650,513 A | 7/1997 | Langhals et al. |
| 6,486,319 B1 | 11/2002 | Bohm et al. |
| 2004/0089199 A1 | 5/2004 | Boehm et al. |
| 2005/0253983 A1 | 11/2005 | Carson et al. |
| 2006/0075585 A1 | 4/2006 | Krieger et al. |

(Continued)

FOREIGN PATENT DOCUMENTS

| | | |
|---|---|---|
| DE | 23 60 705 A1 | 6/1975 |
| DE | 43 38 784 | 5/1995 |

(Continued)

OTHER PUBLICATIONS

Liu, Z. et al. "Amino-substituted rylene dicarboximides and their quinoidal charge delocalization after deprotonation," Chem. Commun. 2008, 5028-5030; Published online Sep. 4, 2008.*

(Continued)

*Primary Examiner* — Yelena G Gakh
*Assistant Examiner* — Michelle Adams
(74) *Attorney, Agent, or Firm* — Oblon, McClelland, Maier & Neustadt, L.L.P.

(57) ABSTRACT

Compounds of the general formula (I)

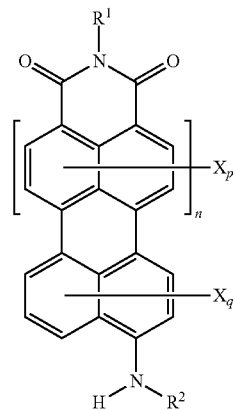

and compounds of the general formula (II)

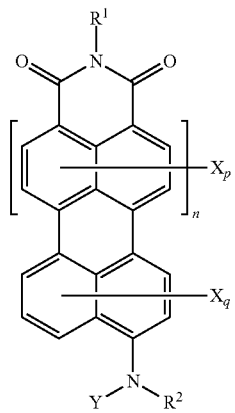

Use of compounds (I) or (II) as visible or invisible markers, for staining materials, in the laser welding of materials, for detecting bases, acids or pH changes, as a dispersing assistant, pigment additive for organic pigments and intermediates for the production of pigment additives, in heat management or energy management, in photovoltaics or in optical data storage.

16 Claims, No Drawings

(56) References Cited

U.S. PATENT DOCUMENTS

2008/0188660 A1    8/2008   Pschirer et al.
2008/0269482 A1   10/2008   Pschirer et al.

FOREIGN PATENT DOCUMENTS

| | | |
|---|---|---|
| EP | 0 596 292 | 5/1994 |
| EP | 0 657 436 | 6/1995 |
| JP | 50-87415 B | 7/1975 |
| JP | 07-188178 A | 7/1995 |
| WO | 01 16109 | 3/2001 |
| WO | 02 066438 | 8/2002 |
| WO | 02 068538 | 9/2002 |
| WO | 2004 026965 | 4/2004 |
| WO | 2004 029028 | 4/2004 |
| WO | 2005 089094 | 9/2005 |
| WO | 2006 111511 | 10/2006 |
| WO | 2006 117383 | 11/2006 |
| WO | 2007 054470 | 5/2007 |

OTHER PUBLICATIONS

"Aryl groups," IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8.*

"Arenes," IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8.*

"Aromatic," IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8.*

International Search Report issued Sep. 9, 2009 in PCT/EP09/056157 filed May 20, 2009.

U.S. Appl. No. 13/322,210, filed Nov. 23, 2011, Sundarraj, et al.

Office Action issued Dec. 9, 2013 in Japanese Patent Application No. 2011-510952 (submitting English language translation only).

Stefan Becker, et al., "New thermotropic dyes based on amino-substituted perylendicarboximides", Chem. Eur. J., vol. 6, No. 21, 2000, pp. 3984-3990.

Michael J. Fuller, et al., "Photorefractivity in nematic liquid crystals using a donor-acceptor dyad with a low-lying excited singlet state for charge generation", J. Phys. Chem. B, vol. 105, No. 30, 2001, pp. 7216-7219.

* cited by examiner

QUINOID RYLENEDICARBOXIMIDES AS IR ABSORBERS

The present invention relates to peri-amino-substituted rylenedicarboximides and to the use thereof.

Further embodiments of the present invention are evident from the claims, the description and the examples. It will be appreciated that the features of the inventive subject matter which have been specified above and which are yet to be explained below can be used not only in the particular combination specified but also in other combinations, without leaving the scope of the invention. Preference and particular preference are given especially also to those embodiments of the present invention in which all features of the inventive subject matter have the preferred and very preferred definitions.

Peryleneimide compounds and their homologs are common knowledge (L. Schmidt-Mende, et al., Science, 2001, 293, 1119; M. A. Angadi, et al., Mat. Sci. Eng., B, 1999, B63, 191).

EP 0 596 292 A1 describes, for example, quaterrylenedicarboximides, processes for preparation thereof and use thereof as fluorescent dyes.

As is well known, perylene- and terrylenebis(dicarboximides) absorb electromagnetic radiation principally in the visible range (F. Holtrup, et al., Chem. Eur. J., 1997, 3, 219-225; F. Nolde et al., Chem. Eur. J., 2005, 11, 3959), while the higher rylene homologs such as quaterrylene-, pentarylene- and hexarylenebis(dicarboximides) absorb in the near infrared (NIR) (H. Quante et al., Angew. Chem. Int. Ed., 1995, 34, 1323, N. G. Pschirer et al., Angew. Chem. 2006, 118, 1429).

WO 02/066438 A1 describes rylene derivatives, processes for preparing the rylene derivatives and the use thereof, for example for coloring high molecular weight organic and inorganic materials, as a dispersing assistant, as pigment additives for organic pigments and intermediates for the preparation of fluorescent dyes and pigment additives. Additionally described is the use of these compounds as a coloring component in decorative cosmetics, for preparation of colored aqueous polymer dispersions or those which absorb and/or emit in the near infrared region of the electromagnetic spectrum, as photoconductors in electronic photography, as emitters in electro- and chemiluminescence applications, as active components in fluorescence conversion and as laser dyes.

WO 04/029028 A1 describes 9-cyano-substituted perylene-3,4-dicarboxylic monoimides, and preparation and use thereof.

In spite of the rylene derivatives already described and the use thereof in connection with their absorption capacity in the NIR spectral region, there is a need for further, especially specifically substituted, derivatives which absorb in the NIR, which are especially simple to prepare and chemically stable.

It was thus an object of the present invention to provide such rylene derivatives which, in particular, have advantages in the synthesis and good properties owing to their stability and their absorption capacity.

This object is achieved by peri-amino-substituted rylenedicarboximides of the formula (I) or mixtures thereof:

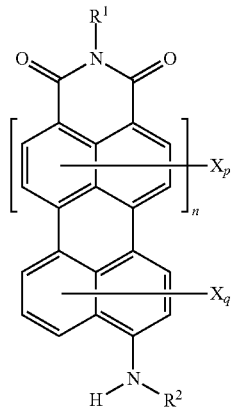

where
$R^1$ is H, $C_1$-$C_{20}$-alkyl, $C_3$-$C_{15}$-cycloalkyl, aryl or hetaryl,
$R^2$ is H, $C_1$-$C_{20}$-alkyl, $C_3$-$C_{15}$-cycloalkyl, aryl or hetaryl,
X is the same or different and is independently halogen, $C_1$-$C_{20}$-alkoxy,
n is 1, 2, 3, 4 or 5
p, q are the same or different and are each independently 0, 1, 2, 3 or 4,
and where the substituents $R^1$ or $R^2$ may each be interrupted at any position by one or more heteroatoms saturated by hydrogen if appropriate, where the number of these heteroatoms is not more than 10, preferably not more than 8, even more preferably not more than 6 and especially not more than 4, and/or may each be substituted at any position, but not more than five times, preferably not more than four times and more preferably not more than three times, by $NR^5R^6$, $CONR^5R^6$, COOM, $COOR^5$, $SO_3M$, $SO_3R^5$,
where
$R^5$, $R^6$ are the same or different and are each independently H, $C_1$-$C_8$-alkyl, aryl,
M is H, alkali metal, $NR^7_4$,
$R^7$ is independently H, $C_1$-$C_8$-alkyl,
CN, $NO_2$, $C_1$-$C_{20}$-alkyl, $C_1$-$C_{20}$-alkoxy, aryl, aryloxy, heterocycles, heteroatoms or halogen, each of which may likewise be substituted not more than twice, preferably not more than once, by the groups specified.

It has been found that the above-described compounds of the general formula (I), after deprotonation on the amine nitrogen in the peri position, have surprisingly intense absorption bands in the NIR spectral region. In addition, these compounds exhibit a high stability, especially in basic media.

In the context of this invention, expressions of the $C_a$-$C_b$ form denote chemical compounds or substituents with a particular number of carbon atoms. The number of carbon atoms can be selected from the entire range from a to b, including a and b, a is at least 1 and b is always greater than a. The chemical compounds or the substituents are specified further by expressions of the $C_a$-$C_b$-V form. V here represents a chemical compound class or substituent class, for example alkyl compounds or alkyl substituents.

In the context of the present invention, infrared radiation (IR radiation for short) refers to electromagnetic waves in the spectral region between visible light and the longer-wavelength microwaves. This corresponds to a wavelength range of from about 760 nm to 1 mm. In the case of short-wave IR radiation (from 760 nm), reference is often made to near infrared (NIR), and at wavelengths of approx.

5-25 micrometers to mid infrared (MIR). Extremely long-wave IR radiation (25 μm-1 mm) is referred to as far infrared (FIR). Infrared radiation is part of thermal radiation.

In the context of the present invention, visible light refers to electromagnetic waves in the spectral region from about 380 nm to 760 nm.

In the context of the present invention, substances which absorb electromagnetic radiation in the wavelength range of IR radiation are also referred to as IR absorbers. IR absorbers preferably have an absorption in the wavelength range from 760 to 2000 nm, very preferably from 780 to 1500 nm, and an extinction coefficient for IR radiation of at least 100 l/(cm*mol). The extinction coefficient for IR radiation is preferably more than 1000 l/(cm*mol) and very preferably more than $10^4$ l/(cm*mol). In the context of the present invention, substances which absorb visible light are also referred to as colored. Colored substances preferably have an extinction coefficient for visible light of at least 100 l/(cm*mol). The extinction coefficient for visible light is preferably more than 1000 l/(cm*mol) and very preferably more than $10^4$ l/(cm*mol).

Halogen is fluorine, chlorine, bromine or iodine, preferably fluorine, chlorine or bromine, more preferably fluorine or chlorine.

Alkali metals are Li, Na or K. In particular, the alkali metals (M) in the chemical-$SO_3M$ or —COOM group may occur as singly positively charged ions.

Specifically, the collective terms specified above for the different are defined as follows:

$C_1$-$C_{20}$-Alkyl: straight-chain or branched hydrocarbon radicals having up to 20 carbon atoms, for example $C_1$-$C_{10}$-alkyl or $C_{11}$-$C_{20}$-alkyl, preferably $C_1$-$C_{10}$-alkyl, for example $C_1$-$C_8$-alkyl, $C_1$-$C_3$-alkyl such as methyl, ethyl, propyl, isopropyl, or $C_4$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl such as heptyl, octyl, 2-ethylhexyl, 2,4,4-trimethylpentyl, 1,1,3,3-tetramethylbutyl, nonyl or decyl, and isomers thereof.

$C_1$-$C_{20}$-Alkoxy is a straight-chain or branched alkyl group having from 1 to 20 carbon atoms (as specified above) which are attached via an oxygen atom (—O—), for example $C_1$-$C_{10}$-alkoxy or $C_{11}$-$C_{20}$-alkoxy, preferably $C_1$-$C_{10}$-alkyloxy, especially preferably $C_1$-$C_3$-alkoxy, for example methoxy, ethoxy, propoxy.

$C_3$-$C_{15}$-Cycloalkyl: monocyclic, saturated hydrocarbon groups having from 3 up to 15 carbon ring members, preferably $C_3$-$C_8$-cycloalkyl such as cyclopropyl, cyclobutyl, cyclopentyl, cyclohexyl, cycloheptyl or cyclooctyl, and a saturated or unsaturated cyclic system, for example norbornyl or norbornenyl.

Aryl: a mono- to tricyclic aromatic ring system comprising from 6 to 14 carbon ring members, for example phenyl, naphthyl or anthracenyl, preferably a mono- to bicyclic, more preferably a monocyclic, aromatic ring system.

Aryloxy is a mono- to tricyclic aromatic ring system (as specified above), which is attached via an oxygen atom (—O—), preferably a mono- to bicyclic, more preferably a monocyclic, aromatic ring system.

Heterocycles (heterocyclic substituents): five- to twelve-membered, preferably five- to nine-membered, more preferably five- to six-membered, ring systems having oxygen, nitrogen and/or sulfur atoms and if appropriate a plurality of rings, such as furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl. The heterocycles may be attached chemically to the compounds of the general formula (I) in any manner, for example via a bond to a carbon atom of the heterocycle or a bond to one of the heteroatoms. In addition, in particular, five- or six-membered saturated nitrogen-containing ring systems which are attached via a ring nitrogen atom and which may also comprise one or two further nitrogen atoms or one further oxygen or sulfur atom.

Hetaryl: Heterocyclic substituents which derive formally from aryl groups by virtue of one or more methine (—C=) and/or vinylene groups (—CH=CH—) being replaced by tri- or divalent heteroatoms. The heteroatoms are preferably oxygen, nitrogen and/or sulfur, more preferably nitrogen and/or oxygen.

$COOR^1$: represents carboxylic acids ($R^1$=H) or carboxylic esters (where, for example, $R^1$=$C_1$-$C_{20}$-alkyl or aryl).

COOM: represents salts of carboxylic acids (for example monovalent alkali metal salts).

$SO_3R^1$: represents sulfonic acids ($R^1$=H) or sulfonic esters (where, for example, $R^1$=$C_1$-$C_{20}$-alkyl or aryl).

$SO_3M$: represents salts of sulfonic acids (for example monovalent alkali metal salts).

$CONR^1R^2$: represents optionally substituted carboxamides. For example, $R^1$ and $R^2$ in this case are the same or different and are each $C_1$-$C_{20}$-alkyl or aryl.

Heteroatoms are phosphorus, oxygen, nitrogen or sulfur, preferably oxygen, nitrogen or sulfur.

Preferably, for the inventive compounds, the symbols in formula (I) are defined as follows:

$R^1$ is $C_1$-$C_{20}$-alkyl, aryl, $R^2$ is aryl,

X is halogen, $C_1$-$C_{20}$-alkoxy, n is 1, 2 or 3, and all other symbols and indices each have the same definition as mentioned at the outset.

More preferably, for the inventive compounds, the symbols in formula (I) are defined as follows:

$R^1$ is $C_1$-$C_{20}$-alkyl, aryl, $R^2$ is aryl,

X are all halogen or $C_1$-$C_{20}$-alkoxy, n is 1, 2 or 3 p, q are the same or different and are each independently 0, 1, 2, and all other symbols and indices have the same definition as mentioned above. Most preferably, p, q are the same or different and are each independently 0 or 2.

The compounds of the general formula (I) can be prepared by methods familiar to those skilled in the art, as described, for example, in T. Edvinsson, et al., J. Phys. Chem. C, 2007, 111, 15137.

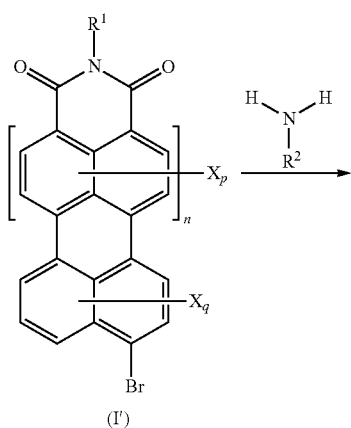

(I')

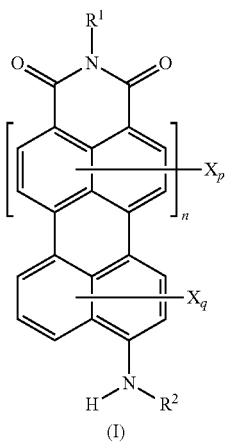

(I)

Processes for preparing the bromide starting compounds (I') are likewise known to those skilled in the art, for example from: WO 2006/117383 A1; F. Holtrup, et al., Chem. Eur. J., 1997, 3, 219-225; F. Nolde et al., Chem. Eur. J., 2005, 11, 3959; H. Quante et al., Angew. Chem. Int. Ed., 1995, 34, 1323; N. G. Pschirer et al., Angew. Chem. 2006, 118, 1429 or Y. Avlasevich, et al., J. Org. Chem., 2007, 72, 10243.

According to the invention, the compounds of the general formula (I) are deprotonated in the peri position on the aminosubstituent using bases.

The invention therefore also provides the compounds of the general formula (II):

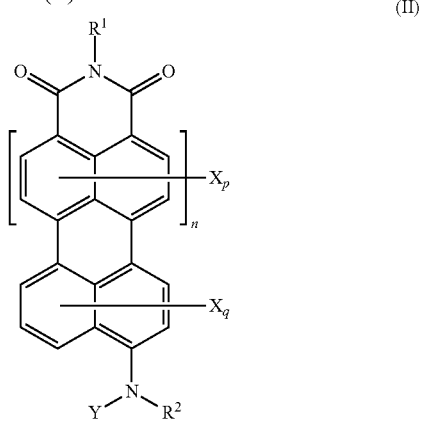

(II)

where
Y is alkali metal, alkaline earth metal, ammonium, alkylammonium, and the other symbols are each as defined at the outset for the compounds of the general formula (I).

Preferably, for the inventive compounds, the symbols in formula (II) are defined as follows:
$R^1$ is $C_1$-$C_{20}$-alkyl, aryl,
$R^2$ is aryl,
X is halogen, $C_1$-$C_{20}$-alkoxy,
n is 1, 2 or 3,
and all other symbols and indices each have the same definition as mentioned above.

More preferably, for the inventive compounds, the symbols in formula (II) are defined as follows:
$R^1$ is $C_1$-$C_{20}$-alkyl, aryl,
$R^2$ is aryl,
X are all halogen or $C_1$-$C_{20}$-alkoxy,
n is 1, 2 or 3
p, q are the same or different and are each independently 0, 1, 2,
and all other symbols and indices have the same definition as mentioned above. Most preferably, p, q are the same or different and are each independently 0 or 2.

The deprotonation of the peri-amino group is generally reversible and can be reversed, for example, with acids. This converts the compounds of the general formula (II) to the corresponding compounds of the general formula (I). It will be appreciated that the inventive compounds may pass through one or more cycles of deprotonation and protonation. One advantage of the inventive compounds (I) and (II) is that they are generally stable to a change in the pH or in the concentration of protons or hydroxide ions, and merely a deprotonation or protonation of the peri-aminosubstituent takes place.

In general, the deprotonation is performed in a solvent or solvent mixture. For example, suitable solvents are polar solvents or mixtures thereof, for example water, tetrahydrofuran, ethanol, 2-propanol, acetone, acetonitrile, dimethylformamide, N-methylpyrrolidone or methylene chloride. Preferred solvents are acetone, tetrahydrofuran, N-methylpyrrolidone or methylene chloride.

The bases used may, for example, be alkali metal hydroxides, such as NaOH, KOH, alkali metal t-butoxides such as t-BuONa, t-BuOK, potassium bis(trimethylsilyl)amide, ammonia or alkylammonium compounds. Preference is given to t-BuONa or t-BuOK.

Particular preference is given to performing the deprotonation in acetone with t-BuONa or t-BuOK.

Compared to the protonated compounds of the general formula (I), the compounds of the general formula (II) have a generally strongly bathochromically shifted absorption spectrum. The absorption of the compounds of the general formula (II) in the NIR spectral region is generally significantly stronger compared to the protonated compounds of the general formula (I).

The compounds of the general formulae (I) and (II) are therefore suitable, for example, as visible or invisible markers.

Preference is given to using the inventive in the marking of paper, mineral oil, plastics or metal surfaces. Particular preference is given to using the compounds of the general formula (I) or (II) as markers for mineral oils or paper. Very preferred is the use for marking paper, especially as a security feature for documents, securities or banknotes.

One advantage of the use as a marker for mineral oils is that mineral oils frequently themselves do not have any absorption in the spectral absorption region of the compounds of the general formula (II), for example in the NIR, and an excellent signal/noise ratio is achieved for the detection even of ultrasmall amounts of the marker, after deprotonation is complete.

Frequently, the compounds of the general formula (I) even absorb visible light and can therefore also be used for staining materials, for example high molecular weight organic and inorganic materials, especially paper, plastics, coating materials or printing inks. This staining can be reduced or eliminated by deprotonation to compounds of the general formula (II), provided that the absorption spectrum of the deprotonated compounds has undergone a bathochromic shift into the IR region.

The invention further provides a process for marking materials, wherein the materials are contacted with compounds of the general formulae (I) and (II). The marking is generally detected visually (with the naked eye) or with the aid of an (absorption) spectrometer.

The inventive marking of paper is effected, for example, by the application of compounds of the general formulae (I) and/or (II) to the surface of the paper to be marked, for example by spraying, impregnating or dropwise application of solutions comprising the inventive compounds of the formulae (I) and (II). In particular, the compounds of the general formulae (I) and (II) can be applied to the paper in a mixture with a printing ink. The amount of compounds of the general formulae (I) and (II) may vary within a wide range according to the application. Preferably less than 10% by weight of compounds of the general formulae (I) and (II) based on the amount of printing ink is used, very preferably less than 5% by weight. The detection of the marking can be undertaken, for example by virtue of a color change, visually or with the aid of an (absorption) spectrometer.

The inventive marking of mineral oil is effected by adding compounds of the general formulae (I) and (II) to the mineral oil to be marked. The amount of compounds of the general formulae (I) and (II) may vary within a wide range according to the application. Preference is given to using fewer than 5 ppm of compounds of the general formulae (I) and (II) based on the amount of mineral oil, very preferably less than 1 ppm. The detection of the marking can be undertaken, for example, optionally after deprotonation using bases, with the aid of an (absorption) spectrometer.

In addition, it is possible to use the inventive compounds of the general formulae (I) and (II) in laser welding.

The invention therefore further provides a process for laser welding of materials, wherein the materials are first contacted with compounds of the general formulae (I) and (II). For welding, in a preferred embodiment, an increase in the IR absorption is brought about in the material by deprotonation, i.e. the inventive compounds of the general formula (II) are, as described below, used as IR absorbers.

The welding of materials, especially of plastics, is effected by absorption of laser energy in or on the plastics material by the laser-sensitive IR absorbers added, which lead to local heating of the material as a result of absorption of laser energy. The laser welding of, for example, two materials generates significant heating in the joining region of the materials to be welded through absorption of the laser energy, such that the materials melt and the two materials fuse together. It is frequently sufficient when only one of the materials comprises laser-sensitive IR absorbers in the material or as a layer on the surface. Laser weldability depends on the nature of the materials, especially plastics, and on the wavelength and the radiative power of the laser used. For example, useful lasers for the process according to the invention for laser welding are $CO_2$, excimer or Nd:YAG lasers.

In general, the content of compounds of the general formulae (I) and (II) is a total of between 0.0001 to 1% by weight based on the material to be welded. The content is preferably from 0.001 to 0.1% by weight. In particular, sufficient weldability of plastics arises within this range from 0.001 to 0.1% by weight.

The compounds of the general formulae (I) and (II) can be processed into virtually all plastics with the aid of processes known to those skilled in the art, for example by extrusion, especially in order to impart laser weldability to them. Typical plastics materials are those in which the plastics matrix is based on poly(meth)acrylate, polyamide, polyurethane, polyolefins, styrene polymers and styrene copolymers, polycarbonate, silicones, polyimides, polysulfone, polyethersulfone, polyketones, polyetherketones, PEEK, polyphenylene sulfide, polyesters (such as PET, PEN, PBT), polyethylene oxide, polyurethane, polyolefins, cycloolefin copolymers or fluorinated polymers (such as PVDF, EFEP, PTFE). Likewise possible is incorporation into blends which comprise abovementioned plastics as components, or into polymers which have been derived from these classes and have been modified by subsequent reactions. These materials are known and commercially available in a wide variety.

The invention further provides for the use of compounds of the general formula (I) for the detection of bases. The bases to be detected result in deprotonation to give the corresponding compounds of the general formula (II) and the detection is effected, for example, by a visually perceptible color change or by the measurement of the changes in the absorption spectrum with the aid of a spectrometer.

The invention further provides for the use of compounds of the general formula (II) for detection of protic acids. The protic acids to be detected result in protonation to give the corresponding compounds of the general formula (I) and the detection is effected, for example, by a visually perceptible color change or by measuring the changes in the absorption spectrum with the aid of a spectrometer.

The present invention further provides for the use of compounds of the general formula (I) or (II) as a dispersing assistant, pigment additive for organic pigments and intermediates for the production of pigment additives.

The present invention further provides for the use of compounds of the general formula (I) or (II) in heat management or energy management.

The present invention further provides for the use of compounds of the general formula (I) or (II) in photovoltaics.

The present invention further provides for the use of compounds of the general formula (I) or (II) in optical data storage.

Frequently, the inventive compounds of the general formulae (I) and (II) are stable even under strongly basic conditions, whereas the imide groups of other rylene dyes undergo ring opening reactions under these conditions.

The deprotonated compounds of the general formula (II) have high extinctions in the NIR spectral region.

The invention is illustrated in detail by the examples without the examples restricting the subject matter of the invention.

EXAMPLES $^1$H, $^{13}$C, H, H COSY and NOE NMR were recorded on Bruker DPX 250, DRX 500 and Avance 700 NMR spectrometers. Infrared spectra were obtained with a Nicolet FT IR320 spectrometer. FD mass spectra were obtained with a VG instrument ZAB 2-SE-FPD instrument. MALDI-TOF were recorded on a Bruker MALDI-TOF spectrometer. UV/Vis/NIR were recorded in 1 cm quartz cuvettes with a Perkin-Elmer Lambda 900 spectrophotometer.

Preparation of Compounds of the General Formula (I):

Example 1

(A) 4-Aminobenzonitrile is reacted with the corresponding peri-bromo compound under Buchwald conditions by Pd catalysis (cf. T. Edvinsson, et al., J. Phys. Chem. C, 2007, 111, 15137). Reagents: 4-aminobenzonitrile, Pd$_2$(dba)$_3$, tris-tert-butylphosphine, t-BuONa, toluene, reaction at 80° C., 12 h. Yield: 84% of theory.

Reaction Under Buchwald Conditions:

The peri-bromo compound (0.18 mmol), 4-aminobenzonitrile (0.36 mmol), tris(dibenzylideneacetone)dipalladium (0) (17 mg, 0.018 mmol), tris-tert-butylphosphine (18 mg, 0.09 mmol), sodium tert-butoxide (67 mg, 0.69 mmol) and dry toluene (10 ml) were stirred at 80° C. under an argon atmosphere overnight. After cooling, the mixture was evaporated off under reduced pressure and then purified by column chromatography (silica gel with dichloromethane as the eluent).

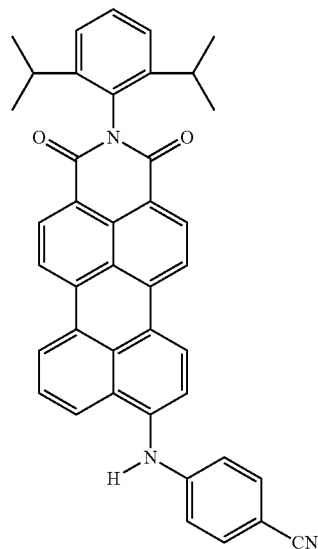

(A)

N-(2,6-diisopropylphenyl)-9-(p-cyanophenylamino) perylene-3,4-dicarboximide (A):

$^1$H NMR (700 MHz, acetone-d$_6$, 50° C.): δ=8.78 (d, J=7.5 Hz, 1H), 8.72 (d, J=8.0 Hz, 1H), 8.70 (d, J=8.3 Hz, 1H), 8.63 (d, J=8.0 Hz, 1H), 8.60 (d, J=8.0 Hz, 1H), 8.58 (d, J=8.0 Hz, 1H), 8.49 (s, 1N-H), 8.35 (d, J=8.4 Hz, 1H), 7.76-7.74 (m, 2H), 7.66 (d, J=8.5 Hz, 2H), 7.44 (t, J=7.9 Hz, 1H), 7.36-7.33 (m, 4H), 2.83 (sep, J=6.8 Hz, 2H), 1.16 ppm (d, J=6.9 Hz, 12H); H,H COSY NMR (700 MHz, acetone-d$_6$, 50° C.): coupling of δ=(8.78, 8.35, 7.76), (8.70, 7.76), (8.72, 8.60), (8.63, 8.58), (7.66, 7.36), (7.44,7.36), (2.83, 1.16); NOE NMR (700 MHz, acetone-d$_6$, 50° C.): coupling of δ=(8.78, 8.72), (8.70, 8.63), (8.49, 7.36), (8.49, 8.35), (7.76, 7.36); $^{13}$C NMR (62.5 MHz, CD$_2$Cl$_2$ 25° C.): δ=164.6, 164.4, 148.0, 146.5, 139.8, 137.8, 134.3, 132.3, 132.12, 132.0, 130.2, 129.7, 128.6, 127.4, 125.7, 125.2, 125.0, 124.7, 124.4, 121.5, 120.8, 120.5, 120.0, 119.7, 118.7, 117.2, 103.6, 29.5, 24.1 ppm. IR: ν=3328, 3064, 2962, 2929, 2867, 2217, 1689, 1644, 1563, 1504, 1351, 1288, 1172, 1058, 971, 910, 804, 750 cm$^{-1}$; UV-Vis (acetone) λ$_{max}$, nm (ε): 550 (34800); MS (FD): m/z, 598.0 (100%), M$^+$;

Elemental analysis: Found: C, 81.75; H, 5.42; N, 6.98%. Calculated for C$_{41}$H$_{31}$N$_3$O$_2$: C, 82.39; H, 5.23; N, 7.03%.

The deprotonated compound (A') corresponding to (A) was obtained in quantitative yield by the reaction with one equivalent of NaOH in acetone at room temperature (20° C.):

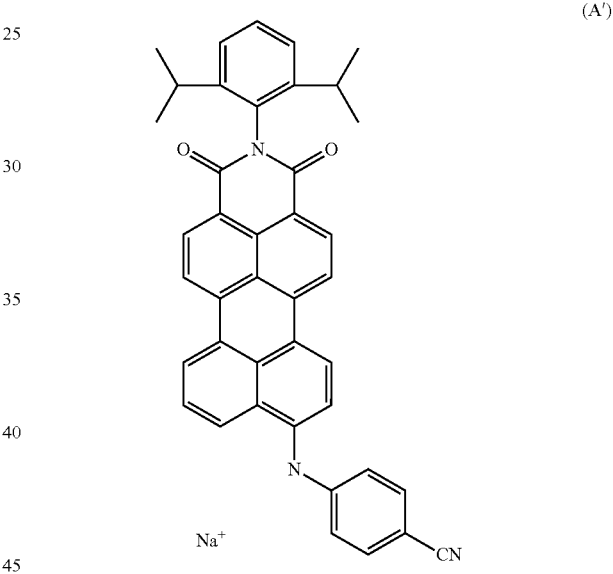

(A')

(A'): $^1$H-NMR (700 MHz, acetone-d$_6$, 25° C.): δ=8.81 (d, J=7.7 Hz, 1H), 8.65 (d, J=7.5 Hz, 1H), 8.29 (d, J=8.3 Hz, 1H), 8.18 (d, J=8.4 Hz, 1H), 8.09 (d, J=8.8 Hz, 1H), 8.06 (d, J=9.7 Hz, 1H), 7.63 (d, J=8.6 Hz, 1H), 7.57 (d, J=8.4 Hz, 2H), 7.45 (t, J=7.7 Hz, 1H), 7.32 (t, J=7.6 Hz, 1H), 7.25 (d, J=7.8 Hz, 2H), 7.10 (d, J=8.4 Hz, 2H), 6.60 (d, J=9.4 Hz, 1H), 2.83 (sep, J=6.8 Hz, 2H), 1.16 ppm (d, J=6.9Hz, 12H); H,H COSY NMR (700 MHz, acetone-d$_6$, 25° C.): coupling of δ=(8.81, 8.65, 7.45), (8.29, 8.18), (8.09, 7.63), (8.06, 6.60), (7.57, 7.10), (7.32, 7.25), (2.83, 1.16); NOE NMR (700 MHz, acetone-d$_6$, 25° C.): coupling of δ=(8.65, 8.18), (8.06, 7.63), (7.10, 6.60).

(A') was convertible quantitatively back to (A) through the use of one equivalent of HCl in acetone at room temperature.

In an analogous manner, the compounds (B) (yield 55%) and (C) (yield 53%) and the corresponding deprotonated compounds (B') and (C') were prepared.

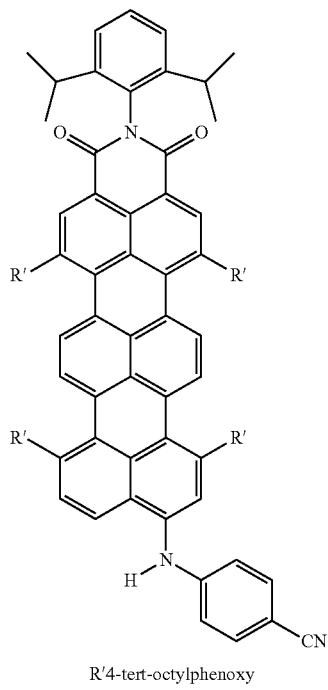

R'4-tert-octylphenoxy (B)

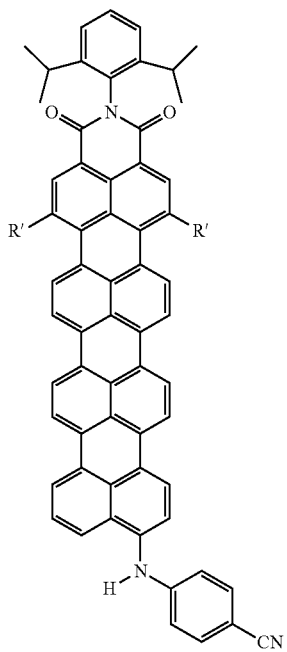

(C)

N-(2,6-Diisopropylphenyl)-1,6,9,14-tetrakis[4-(1,1,3,3-tetramethylbutyl)phenoxy]-11-(p-cyanophenylamino)terrylene-3,4-dicarboximide (B):

$^1$H NMR (250 MHz, acetone-d$_6$, 25° C.): δ=9.50-9.45 (dd, 2H), 9.22-9.13 (dd, 2H) 8.35 (d, J=8.9 Hz, 1H), 8.17 (d, J=8.9 Hz, 1H), 7.68-7.52 (m, 10H), 7.46 (d, J=7.2 Hz, 2H), 7.38-7.28 (m, 7H), 7.39-7.11 (m, 6H), 2.92 (sep, J=6.8 Hz, 2H), 1.95-1.89 (q, 8H), 1.55-1.49 (q, 24H), 1.23-1.19 (q, 12H), 1.01 (d, J=6.9 Hz, 12H), 0.86-0.83 ppm (q, 24H); IR: ν=3326, 3054, 2952, 2923, 2865, 2221, 1698, 1594, 1502, 1365, 1303, 1211, 1170, 1052, 1014, 958, 829, 727 cm$^{-1}$; UV-Vis (acetone) λ$_{max}$, nm (ε): 668 (41900); MS (FD): m/z, 1539.3 (100%), M$^+$.

N-(2,6-Diisopropylphenyl)-1,6-bis[4-(1,1,3,3-tetramethyl-butyl)phenoxy]-13-(p-cyanophenylamino)quaterrylene-3,4-dicarboximid (C):

IR: ν=3359, 3054, 2954, 2925, 2865, 2211, 1693, 1577, 1500, 1384, 1317, 1265, 1209, 1170, 1064, 1014, 806, 744 cm$^{-1}$; UV-Vis (acetone) λ$_{max}$, nm (ε): 751 (51200); MS (FD): m/z, 1255.3 (100%), M$^+$.

The compounds (D) (yield 77%) and (D') were prepared in an analogous manner; instead of 4-aminobenzonitrile, 4-octylaniline was used.

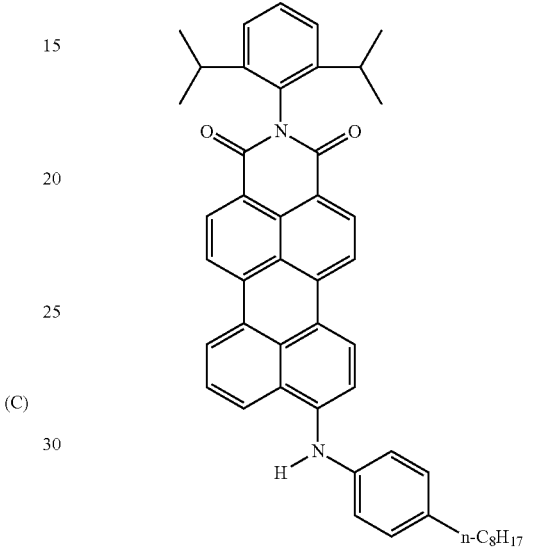

(D)

N-(2,6-Diisopropylphenyl)-9-(p-octylphenylamino) perylene-3,4-dicarboximide (D):

$^1$H NMR (700 MHz, acetone-d$_6$, 50° C.): δ=8.75 (d, J=7.3 Hz, 1H), 8.63 (d, J=8.1 Hz, 1H), 8.55 (d, J=7.9 Hz, 1H), 8.54 (d, J=8.6 Hz, 1H), 8.50 (d, J=8.1 Hz, 1H), 8.48 (d, J=8.5 Hz, 1H), 8.42 (d, J=8.2 Hz, 1H), 8.12 (s, 1N-H), 7.73 (t, J=8.2 Hz, 1H), 7.45 (t, J=7.9 Hz, 1H), 7.38 (d, J=8.5 Hz, 1H), 7.34 (d, J=7.9 Hz, 2H), 7.34 (d, J=8.4 Hz, 2H), 7.29 (d, J=8.4 Hz, 2H), 2.87-2.70 (sep, J=6.8 Hz, 2H), 2.67-2.61 (t, J=7.7 Hz, 2H), 1.68-1.62 (t, J=7.4 Hz, 2H), 1.34-1.30 (m, 10H), 1.18 (d, J=6.9 Hz, 12H), 0.92-0.87 ppm (t, J=7.1 Hz, 3H); H,H COSY NMR (700 MHz, acetone-d$_6$, 50° C.): coupling of δ=(7.73, 8.75, 8.48), (7.38, 8.54), (7.29, 7.34), (7.45, 7.34), (8.50, 8.42), (8.55, 8.63), (2.87, 1.18), (2.67, 1.68), (1.62, 1.34), (1.30, 0.92); $^{13}$C NMR (62.5 MHz, CD$_2$Cl$_2$ 25° C.): δ=164.71, 164.55, 146.52, 144.34, 139.16, 138.96, 138.71, 138.17, 132.27, 131.88, 131.07, 129.97, 129.76, 129.16, 129.56, 129.16, 126.68, 126.47, 126.47, 125.11, 125.02, 124.35, 123.61, 121.84, 120.92, 120.83, 119.88, 118.69, 118.48, 111.08, 35.74, 32.30, 32.06, 29.89, 29.73, 29.69, 29.45, 24.14, 24.10, 23.08, 14.27 ppm. IR: ν=3372, 2964, 2924, 2854, 1690, 1650, 1566, 1514, 1354, 1284, 804, 750 cm$^{-1}$; UV-Vis (acetone) λ$_{max}$, nm (ε): 596 (35233); MS (FD): m/z 683.5 (100%), M$^+$;

Elemental analysis: Found: C, 83.39; H, 7.06; N, 3.96%. Calculated for C$_{48}$H$_{48}$N$_2$O$_2$: C, 84.17; H, 7.06; N, 4.09%.

(D'): $^1$H NMR (250 MHz, acetone-d$_6$, 25° C.): δ=8.83 (d, J=7.6 Hz, 1H), 8.67 (d, J=8.5 Hz, 1H), 8.25 (d, J=8.5 Hz, 1H), 8.11 (d, J=8.7 Hz, 1H), 7.99 (d, J=9.0 Hz, 1H), 7.94 (d, J=10.1 Hz, 1H), 7.48 (d, J=9.0 Hz, 1H), 7.46 (t, J=7.7 Hz, 1H), 7.32 (t, J=7.9 Hz, 1H), 7.25 (d, J=7.9 Hz, 2H), 7.16 (d, J=8.4 Hz, 2H), 6.89 (d, J=8.4 Hz, 2H), 6.52 (d, J=10.0 Hz, 1H), 2.77-2.66 (sep, J=6.9 Hz, 4H), 2.63-2.56 (t, J=7.4 Hz, 2H), 1.64-1.59 (t, J=7.4 Hz, 2H), 1.34-1.30 (m, 10H), 1.13-1.10 (d, J=6.9 Hz, 12H), 0.92-0.86 ppm (t, J=7.0 Hz, 3H); H,H COSY NMR (700 MHz, acetone-$d_6$, 25° C.): coupling of δ=(7.50, 8.83, 8.67), (6.87, 7.12), (6.52, 6.48), (7.35, 7.25), (7.99, 7.48), (8.11, 8.25), (2.77, 1.13), (2.63, 1.64), (1.64, 1.34), (1.30, 0.92).

Example 2

Compound (D) was stable to a treatment with an excess of NaOH in 2-propanol under reflux conditions.

Example 3

$\lambda_{max}$=wavelength of the absorption maximum [nm]
ε: extinction coefficient [$M^{-1}$ $cm^{-1}$]
Absorption maxima of the compounds (A)-(D) and (A')-(D'):

| Compound | $\lambda_{max}$ [nm], (ε) |
|---|---|
| A | 550 (34800) |
| D | 596 (35200) |
| B | 668 (41900) |
| C | 751 (51200) |
| A' | 826 (90400) |
| D' | 780 (70400) |
| B' | 1008 (132200) |
| C' | 1186 (65100) |

Compound D' was stable in an aqueous acetone solution for 3 days and suffered only an intensity loss of 5%.

Repeated titrations (five cycles) of compound D in acetone with aqueous NaOH (0.1 molar) and HCl (0.1 molar) showed the reversibility of the protonation and deprotonation.

The invention claimed is:
1. A compound of formula (II)

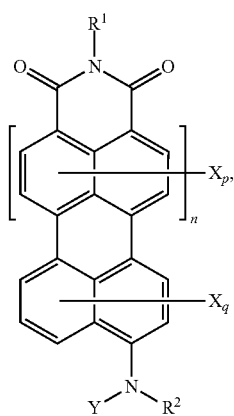

(II)

wherein
Y is a cation selected from the group consisting of an alkali metal and an alkaline earth metal,
$R^1$ is $C_1$-$C_{20}$-alkyl, $C_3$-$C_{15}$-cycloalkyl, aryl, or hetaryl,
$R^2$ is H, $C_1$-$C_{20}$-alkyl, $C_3$-$C_{15}$-cycloalkyl, phenyl, naphthyl, anthracenyl or hetaryl,
X is independently halogen or $C_1$-$C_{20}$-alkoxy,
n is 1, 2, 3, 4, or 5, and
p, q are the same or different and are each independently 0, 1, 2, or 4,
and
wherein when $R^1$ and/or $R^2$ are $C_1$-$C_{20}$-alkyl and or $C_3$-$C_{15}$-cycloalkyl, $R^1$ and/or $R^2$ are optionally interrupted at any position by up to 10 heteroatoms, optionally saturated by hydrogen, and/or $R^1$ and/or $R^2$ are optionally substituted at any position, but not more than five times by at least one of $NR^5R^6$, $CONR^5R^6$, COOM, $COOR^5$, $SO_3M$, $SO_3R^5$, CN, $NO_2$, $C_1$-$C_{20}$-alkyl, $C_1$-$C_{20}$-alkoxy, aryl, aryloxy, a heterocycle, a heteroatom, or a halogen,
wherein
$R^5$, $R^6$ are the same or different and are each independently H, $C_1$-$C_8$-alkyl, or aryl,
M is H, an alkali metal, or $NR^7_4$, and
$R^7$ is independently H, $C_1$-$C_8$-alkyl;
and wherein when the optional substituent of $R^1$ and/or $R^2$ are $C_1$-$C_{20}$-alkyl, $C_1$-$C_{20}$-alkoxy, aryl, aryloxy, heterocycle, and/or heteroatom said optional substituent is optionally substituted, not more than twice by $NR^5R^6$, $CONR^5R^6$, COOM, $COOR^5$, $SO_3M$, $SO_3R^5$, CN, $NO_2$, $C_1$-$C_{20}$-alkyl, $C_1$-$C_{20}$-alkoxy, aryl, aryloxy, a heterocycle, a heteroatom, and/or a halogen
wherein
$R^5$, $R^6$ are the same or different and are each independently H, $C_1$-$C_8$-alkyl, or aryl, and
M is H, an alkali metal, or $NR^7_4$ and
wherein when p and/or q are 1, 2, 3 or 4, X is the same or different.
2. The compound according to claim 1, wherein
$R^1$ is $C_1$-$C_{20}$-alkyl, or aryl,
$R^2$ is phenyl, naphthyl or anthracenyl,
X are all halogen or all $C_1$-$C_{20}$-alkoxy, and
n is 1, 2, or 3.
3. The compound according to claim 1, wherein $R^1$ and/or $R^2$ are interrupted by not more than 8 heteroatoms.
4. The compound according to claim 1, wherein $R^1$ and/or $R^2$ are interrupted by not more than 6 heteroatoms.
5. The compound according to claim 1, wherein $R^1$ and/or $R^2$ are interrupted by not more than 4 heteroatoms.
6. A visible or invisible marker comprising the compound according to claim 1.
7. A process of marking a surface of paper, mineral oil, a plastic, or metal, the process comprising contacting a surface with a composition comprising the compound according to claim 1.
8. A process of staining a material, the process comprising applying the compound according to claim 1 or a composition comprising the compound of claim 1 to the material.
9. The process according to claim 8, wherein the material is a high molecular weight organic or inorganic material.
10. A process for marking a material, the process comprises contacting the material with the compound according to claim 1.
11. A process for laser welding a material, the process comprising:
first, contacting the material with the compound according to claim 1, which serves as an IR absorber; and
then, irradiating the material with a laser whose emitted wavelength overlaps with an absorption region of the IR absorber.
12. A process of detecting a base, an acid, or pH change, the process comprising contacting the compound according to claim 1 with a solution.
13. A dispersion or pigment precursor, comprising the compound according to claim 1.

14. An insulation or heat or energy management material, comprising the compound according to claim 1.

15. A photovoltaic, comprising the compound according to claim 1.

16. An optical data storage device, comprising the according to claim 1.

* * * * *